United States Patent
Sasai et al.

(10) Patent No.: US 9,061,143 B2
(45) Date of Patent: Jun. 23, 2015

(54) CHARGED PARTICLE BEAM IRRADIATION SYSTEM AND CHARGED PARTICLE BEAM IRRADIATION PLANNING METHOD

(71) Applicants: Sumitomo Heavy Industries, Ltd., Tokyo (JP); National Cancer Center, Tokyo (JP)

(72) Inventors: Kenzo Sasai, Niihama (JP); Teiji Nishio, Kashiwa (JP)

(73) Assignees: SUMITOMO HEAVY INDUSTRIES, LTD., Tokyo (JP); NATIONAL CANCER CENTER, Tokyo (JP)

(*) Notice: Subject to any disclaimer, the term of this patent is extended or adjusted under 35 U.S.C. 154(b) by 0 days.

(21) Appl. No.: 14/350,861

(22) PCT Filed: Oct. 9, 2012

(86) PCT No.: PCT/JP2012/076128
§ 371 (c)(1),
(2) Date: Apr. 10, 2014

(87) PCT Pub. No.: WO2013/054788
PCT Pub. Date: Apr. 18, 2013

(65) Prior Publication Data
US 2014/0252227 A1     Sep. 11, 2014

(30) Foreign Application Priority Data

Oct. 14, 2011  (JP) ................................. 2011-227080

(51) Int. Cl.
*A61N 5/10* (2006.01)
*G21K 1/04* (2006.01)
*G21K 1/10* (2006.01)

(52) U.S. Cl.
CPC .............. *A61N 5/1031* (2013.01); *G21K 1/046* (2013.01); *G21K 1/10* (2013.01); *A61N 2005/1087* (2013.01)

(58) Field of Classification Search
USPC ............ 250/306, 307, 492.1, 492.21, 492.22, 250/492.3; 514/256, 385, 396; 382/128, 382/132
See application file for complete search history.

(56) References Cited

U.S. PATENT DOCUMENTS 3,691,376 A * 9/1972 Bauerlein et al. ............. 438/351
3,829,961 A * 8/1974 Bauerlein et al. ............. 438/351

(Continued)

FOREIGN PATENT DOCUMENTS

JP   2006-280457 A   10/2006
JP   2008-545468 A   12/2008

(Continued)

OTHER PUBLICATIONS

International Search Report dated Nov. 13, 2012 corresponding to International Patent Application No. PCT/JP2012/076128.

(Continued)

*Primary Examiner* — Bernard E Souw
(74) *Attorney, Agent, or Firm* — Squire Patton Boggs (US) LLP

(57) ABSTRACT

A charged particle beam irradiation system includes: an irradiation unit configured to irradiate an irradiation target with a charged particle beam; a radiation resistance state measuring section configured to measure a radiation resistance state of the irradiation target; a region dividing section configured to divide the irradiation target into a plurality of radiation resistance regions based on a measurement result of the radiation resistance state measuring section; a radiation dose computing section configured to compute a planned value of a radiation dose of the charged particle beam for each of the plurality of radiation resistance regions divided by the region dividing section; and an irradiation planning section-configured to create an irradiation plan of the charged particle beam with respect to the irradiation target based on a computation result of the radiation dose computing section.

14 Claims, 13 Drawing Sheets

(56) References Cited

U.S. PATENT DOCUMENTS

| | | | |
|---|---|---|---|
| 7,247,501 B2 * | 7/2007 | Kim et al. | 436/520 |
| 8,129,468 B2 * | 3/2012 | Simon | 524/863 |
| 8,148,381 B2 * | 4/2012 | Fukushima | 514/256 |
| 8,170,308 B2 * | 5/2012 | Fischer et al. | 382/128 |
| 2004/0057940 A1 * | 3/2004 | Kim et al. | 424/93.21 |
| 2009/0208075 A1 * | 8/2009 | Fischer et al. | 382/128 |
| 2009/0286755 A1 * | 11/2009 | Fukushima | 514/50 |
| 2012/0068631 A1 * | 3/2012 | Nishio et al. | 315/500 |
| 2013/0087721 A1 * | 4/2013 | Nishio et al. | 250/492.3 |

FOREIGN PATENT DOCUMENTS

| | | |
|---|---|---|
| JP | 2009-525114 A | 7/2009 |
| JP | 2010-523596 A | 7/2010 |
| JP | 2011-212078 A | 10/2011 |

OTHER PUBLICATIONS

International Preliminary Report on Patentability application No. PCT/JP2012/076128 dated Apr. 15, 2014.

* cited by examiner

Fig.7
(a)
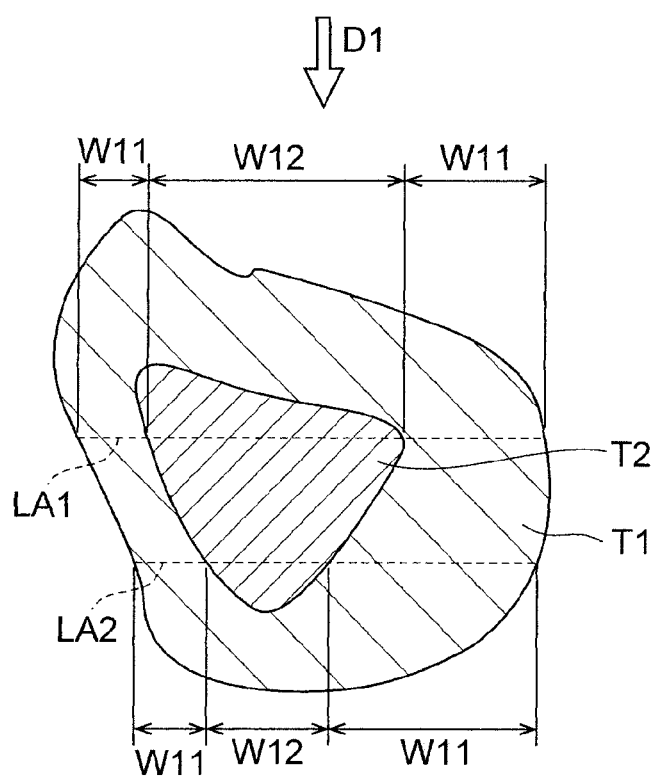
(b)
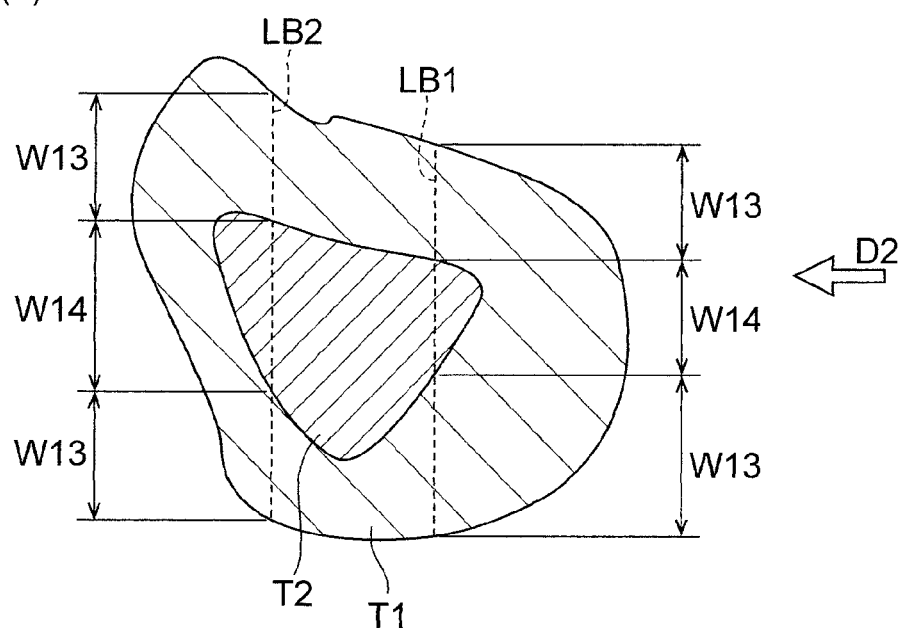

CHARGED PARTICLE BEAM IRRADIATION SYSTEM AND CHARGED PARTICLE BEAM IRRADIATION PLANNING METHOD

INCORPORATION BY REFERENCE

Priority is claimed to Japanese Patent Application No. 2011.227080, filed Oct. 14, 2011, and International Patent Application No. PCT/JP2012/076128, the entire content of each of which is incorporated herein by reference.

BACKGROUND

1. Technical Field

The present invention relates to a charged particle beam irradiation system and a charged particle beam irradiation planning method.

2. Description of the Related Art

In radiation therapy using a charged particle beam, it is necessary to create an accurate therapy plan based on the shape and position of a tumor of a patient. For example, the related art discloses a method of creating a therapy plan based on irradiation of a charged particle beam after obtaining imaging information on the interior of the body of a patient and discriminating between a lesion tissue and a normal tissue of the interior of the body based on the imaging information.

SUMMARY

According to an embodiment of the present invention, there is provided a charged particle beam irradiation system including: an irradiation unit configured to irradiate an irradiation target with a charged particle beam; a radiation resistance state measuring section configured to measure a radiation resistance state of the irradiation target; a region dividing section configured to divide the irradiation target into a plurality of radiation resistance regions based on a measurement result of the radiation resistance state measuring section; a radiation dose computing section configured to compute a planned value of a radiation dose of the charged particle beam for each of the plurality of radiation resistance regions divided by the region dividing section; and an irradiation planning section configured to create an irradiation plan of the charged particle beam with respect to the irradiation target based on a computation result of the radiation dose computing section.

According to another embodiment of the present invention, there is provided a charged particle beam irradiation planning method including: a radiation resistance state measuring step of measuring a radiation resistance state of an irradiation target; a region dividing step of dividing the irradiation target into a plurality of radiation resistance regions based on a measurement result of the radiation resistance state measuring step; a radiation dose computing step of computing a planned value of a radiation dose of a charged particle beam for each of the plurality of radiation resistance regions divided in the region dividing step; and an irradiation planning step of creating the irradiation plan of the charged particle beam with respect to the irradiation target based on a computation result of the radiation dose computing step.

BRIEF DESCRIPTION OF THE DRAWINGS

FIG. 7A is a diagram illustrating intensity-modulated ion therapy based on radiation resistance in a direction D1, and FIG. 7B is a diagram illustrating intensity-modulated ion therapy based on radiation resistance in a direction D2.

DETAILED DESCRIPTION

Figure 1:
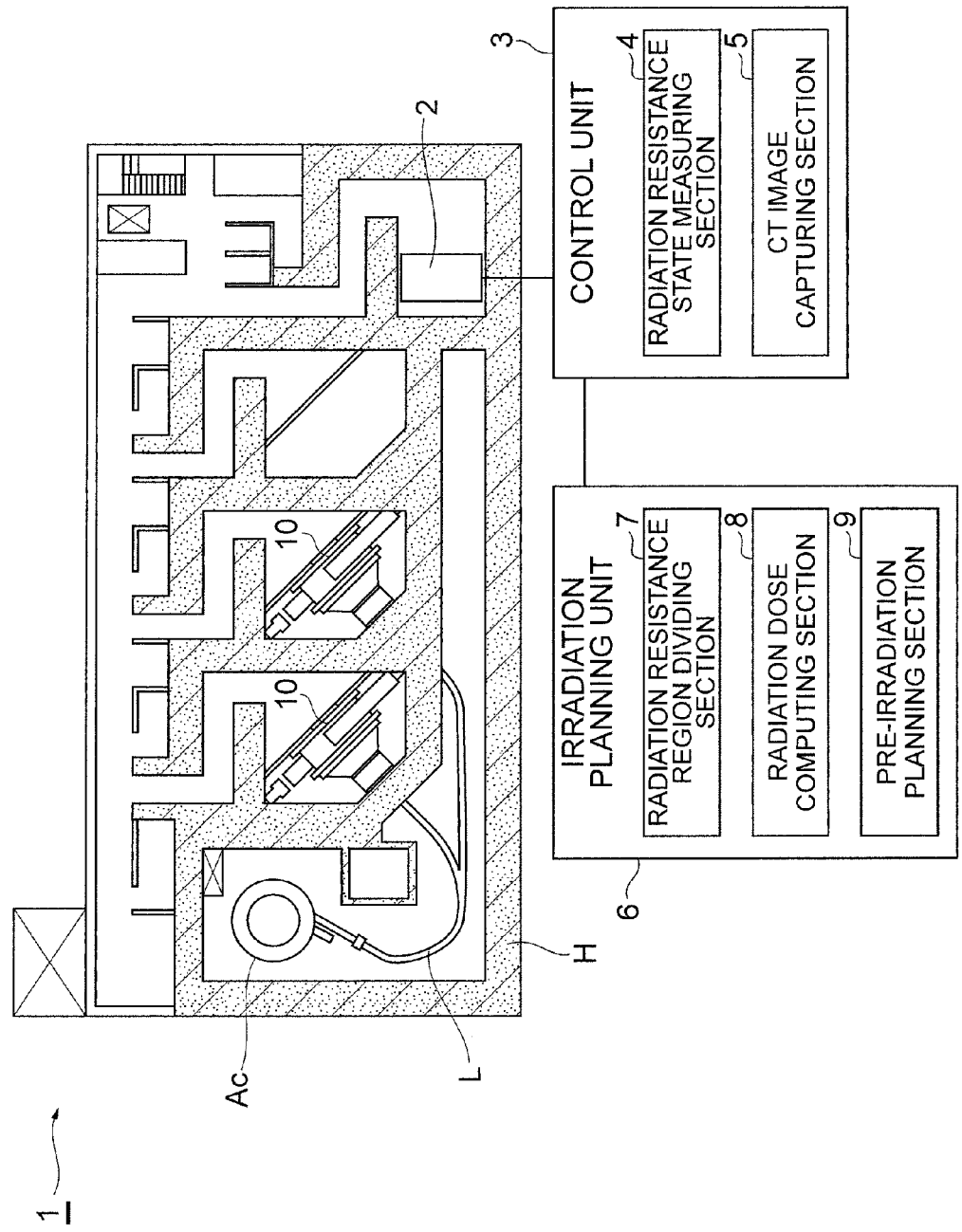
FIG. 1 is a diagram schematically illustrating a charged particle beam irradiation system according to one embodiment.

However, a tumor such as a cancer may contain a portion having high radiation resistance such as a hypoxic cell. In this case, even though the entire affected part is irradiated with a charged particle beam of a uniform radiation dose, the therapy efficiency is low, and thus, it is difficult to obtain a sufficient effect. Thus, it is necessary to realize effective radiation irradiation in consideration of a case where a portion having high radiation resistance is present in the affected part.

Accordingly, it is desirable to provide a charged particle beam irradiation system and a charged particle beam irradiation planning method capable of creating a charged particle beam irradiation plan in consideration of radiation resistance.

According to the charged particle beam irradiation system, since the radiation dose for irradiation of the irradiation target is changed according to the level of radiation resistance (radiation resistance state), by dividing the irradiation target into the plural regions according to the level of the radiation resistance, it is possible to compute a planned value of an appropriated radiation dose for each region, to create an effective irradiation plan of the charged particle beam. Accordingly, in this charged particle beam irradiation system, it is possible to create an effective charged particle beam irradiation plan in consideration of the radiation resistance based on the planned value of the radiation dose computed for each region.

The charged particle beam irradiation system according to the present embodiment may further include a pre-irradiation planning section configured to create a pre-irradiation plan of the charged particle beam with respect to the irradiation target based on a captured image of the irradiation target, and the irradiation planning section may correct the pre-irradiation plan based on the computation result of the radiation dose computing section to create the irradiation plan.

According to the charged particle beam irradiation system having such a configuration, the pre-irradiation plan is created in advance based on the captured image of the irradiation target obtained in advance by a computed tomography (CT) scan or the like. Then, by measuring the radiation resistance state of the irradiation target at a point in time when it is actually irradiated with the charged particle beam, it is possible to correct the pre-irradiation plan based on the planned value of the radiation dose computed for each region based on the radiation resistance state to create an actual irradiation plan. Accordingly, in this charged particle beam irradiation system, it is possible to reflect the radiation resistance state of the irradiation target at the point in time when it is actually irradiated with the charged particle beam into the irradiation plan, to thus create an effective charged particle beam irradiation plan in consideration of the radiation resistance.

Alternatively, in the charged particle beam irradiation system according to the present embodiment, the irradiation planning section may create the irradiation plan based on a captured image of the irradiation target and the computation result of the radiation dose computing section.

According to the charged particle beam irradiation system having such a configuration, by creating an actual irradiation plan in detail in advance based on the planned value of the radiation dose for each region computed from the radiation resistance state of the irradiation target by a position emission tomography (PET) scan or the like and the captured image of the irradiation target obtained in advance by the CT scan or the like, even when an inspection device for PET or the like is installed in a room other than an irradiation room, it is possible to create an effective charged particle beam irradiation plan in consideration of the radiation resistance.

In the charged particle beam irradiation system according to the present embodiment, the radiation resistance state measuring section may include a gamma-ray detector, and the region dividing section may divide the irradiation target into the plurality of radiation resistance regions based on a measurement result of the gamma-ray detector that uses FMISO as a tracer.

According to the charged particle beam irradiation system having such a configuration, by detecting the accumulation of FMISO using the gamma-ray detector, it is possible to measure the presence or absence or distribution of a hypoxic cell with high radiation resistance compared with a normal lesion cell. Accordingly, in this charged particle beam irradiation system, it is possible to perform the region division of the irradiation target according to the level of the radiation resistance with reference to the presence or absence, distribution or the like of the hypoxic cell.

In the charged particle beam irradiation system according to the present embodiment, the radiation resistance state measuring section may include a gamma-ray detector, and the region dividing section may divide the irradiation target into the plurality of radiation resistance regions based on a measurement result of the gamma-ray detector that uses FAZA as a tracer.

According to the charged particle beam irradiation system having such a configuration, by detecting the accumulation of FAZA using the gamma-ray detector, it is possible to measure the position or the like of a hypoxic cell with high radiation resistance compared with a normal lesion cell. Accordingly, in this charged particle beam irradiation system, it is possible to perform the region division of the irradiation target according to the level of the radiation resistance with reference to the presence or absence, distribution or the like of the hypoxic cell. Further, by using FAZA having low fat-solubility and quick blood clearance compared with FMISO as the tracer, it is possible to efficiently perform the measurement of the hypoxic cell.

In the charged particle beam irradiation system according to the present embodiment, the radiation resistance state measuring section may include a gamma-ray detector, and the region dividing section may divide the irradiation target into the plurality of radiation resistance regions based on a measurement result of the gamma-ray detector that uses IAZA as a tracer.

According to the charged particle beam irradiation system having such a configuration, by detecting the accumulation of IAZA using the gamma-ray detector, it is possible to measure the position or the like of a hypoxic cell with high radiation resistance compared with a normal lesion cell. Accordingly, in this charged particle beam irradiation system, it is possible to perform the region division of the irradiation target according to the level of the radiation resistance with reference to the presence or absence, distribution or the like of the hypoxic cell.

In the charged particle beam irradiation system according to the present embodiment, the radiation resistance state measuring section may include a gamma-ray detector, and the region dividing section may divide the irradiation target into the plurality of radiation resistance regions based on a measurement result of the gamma-ray detector that uses FETNIM as a tracer.

According to the charged particle beam irradiation system having such a configuration, by detecting the accumulation of FETNIM using the gamma-ray detector, it is possible to measure the position or the like of a hypoxic cell with high radiation resistance compared with a normal lesion cell. Accordingly, in this charged particle beam irradiation system, it is possible to perform the region division of the irradiation target according to the level of the radiation resistance with reference to the presence or absence, distribution or the like of the hypoxic cell.

According to the charged particle beam irradiation planning method, since the radiation dose for irradiation of the irradiation target is changed according to the level of radiation resistance (radiation resistance state), by dividing the irradiation target into the plural regions based on the level of the radiation resistance, it is possible to compute an appropriated radiation dose for each region, to create an effective irradiation plan of the charged particle beam. Accordingly, in this charged particle beam irradiation planning method, it is possible to create an irradiation plan of the charged particle with an excellent therapy effect in consideration of the radiation resistance based on the radiation dose computed for each region.

The charged particle beam irradiation planning method according to the present embodiment may include a pre-irradiation planning step of creating a pre-irradiation plan of the charged particle beam with respect to the irradiation target based on a captured image of the irradiation target before the radiation resistance state measuring step, and in the irradiation planning step, the pre-irradiation plan may be corrected based on the computation result of the radiation dose computing step to create the irradiation plan.

According to the charged particle beam irradiation planning method having such a configuration, the pre-irradiation plan is created in advance based on the captured image of the irradiation target obtained in advance by a computed tomography (CT) scan or the like. Then, by measuring the radiation resistance state of the irradiation target at a point in time when it is actually irradiated with the charged particle beam, it is possible to correct the pre-irradiation plan based on the planned value of the radiation dose computed for each region based on the radiation resistance state, and to create an actual irradiation plan. Accordingly, in this charged particle beam irradiation planning method, it is possible to reflect the radiation resistance state of the irradiation target at the point in time when it is actually irradiated with the charged particle beam into the irradiation plan, to thus create an effective charged particle beam irradiation plan in consideration of the radiation resistance.

Alternatively, in the charged particle beam irradiation planning method according to the present embodiment, in the irradiation planning step, the irradiation plan may be created based on a captured image of the irradiation target and the computation result of the radiation dose computing step.

According to the charged particle beam irradiation planning method having such a configuration, by creating an actual irradiation plan in detail in advance based on the planned value of the radiation dose for each region computed from the radiation resistance state of the irradiation target by a positron emission tomography (PET) scan or the like and the captured image of the irradiation target obtained in advance by the CT scan or the like, even when an inspection device for PET or the like is installed in a room other than an irradiation room, it is possible to create an effective charged particle beam irradiation plan in consideration of the radiation resistance.

In the charged particle beam irradiation planning method according to the present embodiment, in the radiation resistance state measuring step, the radiation resistance state of the irradiation target may be measured based on a gamma-ray detection that uses FMISO as a tracer.

According to the charged particle beam irradiation planning method having such a configuration, by detecting the accumulation of FMISO using the gamma-ray detector, it is possible to measure the position or the like of a hypoxic cell with high radiation resistance compared with a normal lesion cell. Accordingly, in this charged particle beam irradiation planning method, it is possible to perform the region division of the irradiation target according to the level of the radiation resistance with reference to the presence or absence, distribution or the like of the hypoxic cell.

In the charged particle beam irradiation planning method according to the present embodiment, in the radiation resistance state measuring step, the radiation resistance state of the irradiation target may be measured based on a gamma-ray detection that uses FAZA as a tracer.

According to the charged particle beam irradiation planning method having such a configuration, by detecting the accumulation of FAZA using the gamma-ray detector, it is possible to measure the position or the like of a hypoxic cell with high radiation resistance compared with a normal lesion cell. Accordingly, in this charged particle beam irradiation planning method, it is possible to perform the region division of the irradiation target according to the level of the radiation resistance with reference to the presence or absence, distribution or the like of the hypoxic cell. Further, by using FAZA having low fat-solubility and quick blood clearance compared with FMISO as the tracer, it is possible to efficiently perform the measurement of the hypoxic cell.

In the charged particle beam irradiation planning method according to the present embodiment, in the radiation resistance state measuring step, the radiation resistance state of the irradiation target may be measured based on a gamma-ray detection that uses IAZA as a tracer.

According to the charged particle beam irradiation planning method having such a configuration, by detecting the accumulation of IAZA using the gamma-ray detector, it is possible to measure the position or the like of a hypoxic cell with high radiation resistance compared with a normal lesion cell. Accordingly, in this charged particle beam irradiation planning method, it is possible to perform the region division of the irradiation target according to the level of the radiation resistance with reference to the presence or absence, distribution or the like of the hypoxic cell.

In the charged particle beam irradiation planning method according to the present embodiment, in the radiation resistance state measuring step, the radiation resistance state of the irradiation target may be measured based on a gamma-ray detection that uses FETNIM as a tracer.

According to the charged particle beam irradiation planning method having such a configuration, by detecting the accumulation of FETNIM using the gamma-ray detector, it is possible to measure the position or the like of a hypoxic cell with high radiation resistance compared with a normal lesion cell. Accordingly, in this charged particle beam irradiation planning method, it is possible to perform the region division of the irradiation target according to the level of the radiation resistance with reference to the presence or absence, distribution or the like of the hypoxic cell.

Hereinafter, preferred embodiments of the present invention will be described in detail with reference to the accompanying drawings.

First Embodiment

As shown in FIG. 1, a charged particle beam irradiation system 1 according to a first embodiment includes a positron emission tomography-computed tomography (PET-CT) device 2 that inspects a tumor (irradiation target) A of a patient, and a charged particle beam irradiation device 10 that performs charged particle beam irradiation using an inspection result of the PET-CT device 2. These devices are accommodated in a room H.

A gamma-ray detector such as a positron emission tomography (PET) device or a positron emission tomography-magnetic resonance imaging (PET-MRI) device, and a CT device may be provided instead of the PET-CT device 2.

Further, an accelerator Ac that accelerates a charged particle to emit a charged particle beam, and a beam transportation line L that transports the charged particle beam emitted from the accelerator Ac to the charged particle beam irradiation device 10 are disposed in the room H.

As the accelerator Ac, for example, a cyclotron, a synchrotron, a synchrocyclotron, a linear accelerator or the like may be employed. The charged particle beam (for example, a proton beam) accelerated by the accelerator Ac is deflected along the beam transportation line L, and is then supplied to the charged particle beam irradiation device 10. A deflection electromagnet that deflects the charged particle beam, a quadrupole electromagnet that performs beam shaping of the charged particle beam, or the like is provided in the beam transportation line L.

The PET-CT device 2 is a device that performs a CT scan and a PET scan of the tumor A before therapy using the charged particle beam. Such scans are performed several days before the therapy using the charged particle beam is performed. The PET-CT device 2 is controlled by a control unit 3.

The control unit 3 is a computer that includes an electronic control unit provided with a central processing unit (CPU), a read only memory (ROM), a random access memory (RAM) and the like. The control unit 3 may include a single computer, or may include plural computers.

The control unit 3 includes a radiation resistance state measuring section 4 and a CT image capturing section 5. The radiation resistance state measuring section 4 controls the PET-CT device 2 to measure a radiation resistance state of the tumor A of the patient.

Specifically, the radiation resistance state measuring section 4 detects a gamma-ray emitted according to collapse of a radioactive tracer administered to the patient using the PET-CT device 2 to measure the position of a lesion cell of the tumor A where the radioactive tracer is accumulated. As the radioactive tracer, FMISO ($[^{18}F]$ misonidazole), FAZA ($[^{18}F]$ fluoroazomycin arabinoside), FETNIM ($[^{18}F]$ fluoroerythronitroimidazole), IAZA ($[^{123/124}I]$ iodoazomycin arabinoside), FETA ($[^{18}F]$ fluoroetanidazole), ATSM ($[^{64}Cu]$ diacetyl-bis(N(4)-methylthiosemicarbazone), β-5-FAZR (1-β-D-(5-fluoro-5-deoxyribofuranosyl)-2-nitroimidazole transport), $[^{18}F]$ EF5, $[^{18}F]$ EF3, $[^{18}F]$ FDG or the like is known. Here, a case where FMISO is used as the radioactive tracer will be described.

A cancer that is a malignant tumor does not need sufficient oxygen in its multiplication and is thus in a hypoxic state. Further, it is known that a cell (hypoxic cell) in the hypoxic state has resistance to radiation therapy. If FMISO is administered to the patient, FMISO is accumulated in the hypoxic cell that is present in the caner and emits a gamma-ray by being collapsed. By detecting the gamma-ray, the radiation resistance state measuring section 4 can measure the position, shape and the like of the hypoxic cell with high radiation resistance. The radiation resistance state measuring section 4 measures the radiation resistance state of the tumor A including the position, shape and the like of the hypoxic cell.

The CT image capturing section 5 controls the PET-CT device 2 to perform tomography of the tumor A of the patient. The CT image capturing section 5 captures a tomogram (CT image) of the tumor A using an X-ray or the like. It is possible to confirm the position, size and shape of the tumor A from the tomogram obtained by the CT image capturing section 5.

When a gamma-ray detector and a CT device are separately provided instead of the PET-CT device 2, the CT image capturing section 5 is provided in a control unit for the CT device, instead of the control unit for the gamma-ray detector. Here, when one control unit 3 controls both of the gamma-ray detector and the CT device that are separately provided (when the control unit for the gamma-ray detector and the control unit for the CT device are integrally formed), the CT image capturing section 5 may be provided in the control unit 3.

The control unit 3 is connected for data communication to an irradiation planning unit (therapy planning unit) 6 that creates a pre-irradiation plan of the charged particle beam with respect to the tumor A. The pre-irradiation plan refers to a plan created at a previous stage of an irradiation plan that is executed in practice.

The irradiation planning unit 6 creates the pre-irradiation plan based on the radiation resistance state of the tumor A measured by the radiation resistance state measuring section 4 and the captured image of the tumor A captured by the CT image capturing section 5. The irradiation planning unit 6 is a separate unit provided in a room different from the charged particle beam irradiation device 10.

The irradiation planning unit 6 includes a radiation resistance region dividing section 7, a radiation dose computing section 8 and a pre-irradiation planning section (pre-irradiation planning means) 9. The radiation resistance region dividing section 7 divides the tumor A into a normal radiation resistance region T1 and a high radiation resistance region T2 based on the measurement result of the radiation resistance state measuring section 4 and the tomogram of the tumor A captured by the CT image capturing section 5 (see FIG. 2). In the present embodiment, a region that does not include the hypoxic cell is referred to as the normal radiation resistance region T1, and a region that includes the hypoxic cell is referred to as the high radiation resistance region T2. In the present embodiment, the tumor may be divided into two regions according to the presence or absence of the hypoxic cell, but the tumor A may be divided into three or more radiation resistance regions according to a distribution density of the hypoxic cells.

The radiation dose computing section 8 computes a planned radiation dose necessary for therapy of each of the regions T1 and T2 divided by the radiation resistance region dividing section 7. The radiation dose computing section 8 performs the computation so that a planned value of the radiation dose of the high radiation resistance region T2 is larger than a planned radiation dose of the normal radiation resistance region T1. The radiation dose computing section 8 computes the planned radiation dose based on the shape and the like of the tumor A obtained from the tomogram of the tumor A.

The pre-irradiation planning section 9 creates a pre-irradiation plan based on the computation result of the radiation dose computing section 8 and the shape or the like of the tumor A obtained from the tomogram of the tumor A. The pre-irradiation planning section 9 computes an irradiation angle of the charged particle beam, the number of irradiations, a scan rate of the charged particle beam, and the like with respect to the tumor A so as to satisfy the planned radiation dose computed by the radiation dose computing section 8. Further, the pre-irradiation planning section 9 plans an intensity-modulated ion therapy (IMIT).

The intensity-modulated ion therapy is an irradiation method of irradiating the tumor A with the charged particle beam in plural directions. In the intensity-modulated ion therapy, when the irradiation of the charged particle beam is performed in a certain direction, the radiation dose of the charged particle beam is changed for each predetermined region in an irradiation field so that the radiation dose of the charged particle beam in the irradiation field is not uniform. Further, similarly, when the irradiation of the charged particle beam is performed in a different direction, the radiation dose of the charged particle beam is changed for each predetermined region in an irradiation field. Here, the irradiation field refers to a range of the affected part such as the tumor A that is irradiated with the charged particle beam, when seen in the irradiation direction of the charged particle beam.

Figure 3:
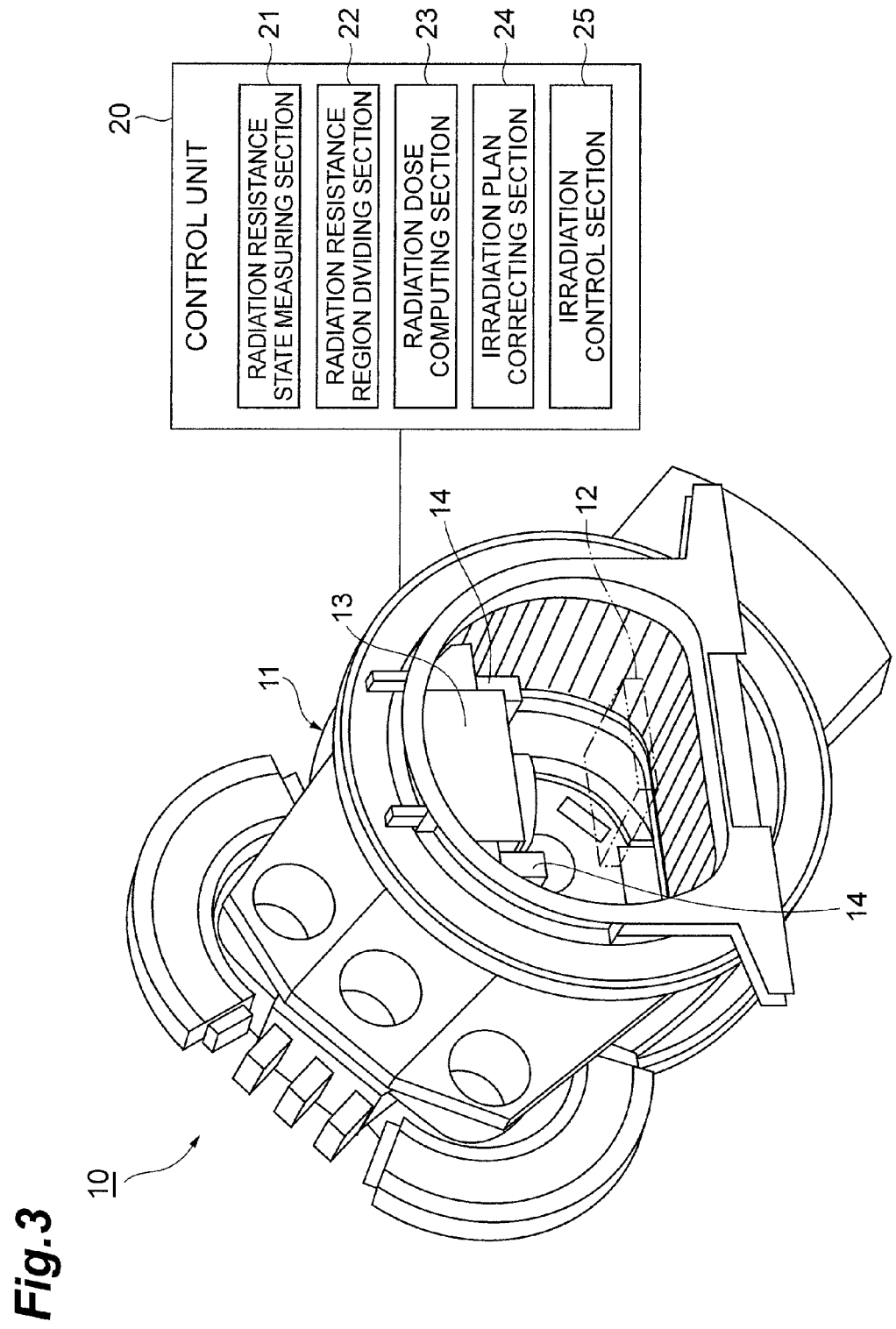
FIG. 3 is a perspective view illustrating a charged particle beam irradiation device in FIG. 1.

Next, the charged particle beam irradiation device 10 that performs the irradiation of the charged particle beam in practice will be described. As shown in FIG. 3, the charged particle beam irradiation device 10 includes a gantry 11 provided to surround a treatment stand 12. The gantry 11 is configured to be rotatable around the treatment stand 12. In the gantry 11, an irradiation unit (irradiation nozzle) 13 that irradiates the tumor A of the patient on the treatment stand 12 with the charged particle beam is provided, in which the irradiation angle of the charged particle beam with respect to the tumor A may be changed by the rotation of the gantry 11.

Figure 4:
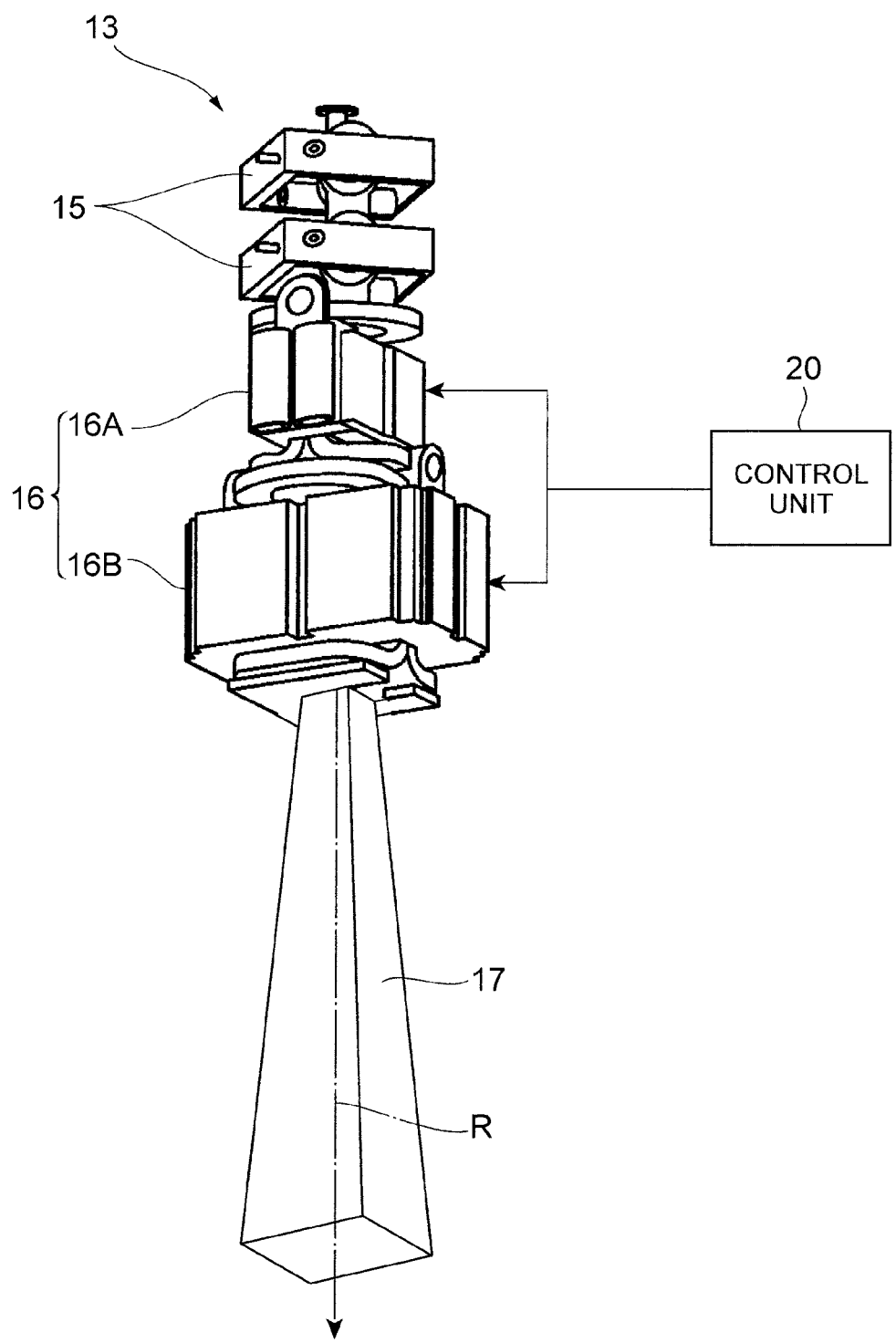
FIG. 4 is a diagram illustrating a configuration of an irradiation unit in FIG. 3.

The irradiation unit 13 shown in FIG. 4 is an irradiation nozzle for a so-called scanning type. The irradiation unit 13 divides the tumor A into plural layers in a depth direction and performs continuous irradiation (so-called raster scanning or line scanning) while scanning the charged particle beam in the irradiation field set in each layer. The charged particle beam emitted from the irradiation unit 13 is indicated as a reference sign R.

The irradiation unit 13 includes a quadrupole magnet 15 that suppresses dispersion of the charged particle beams incident through the beam transportation line L to converge the charged particle beams, a scanning electromagnet 16 that scans the charged particle beam in an X axis direction and a Y axis direction, and a duct 17 through which the charged particle beams pass. The X axis direction and the Y axis direction refer to directions that are orthogonal to each other in a plane vertical to a traveling direction of the charged particle beam.

The scanning electromagnet 16 includes a set of electromagnets 16A that controls the irradiation position of the charged particle beam in the X axis direction, and a set of electromagnets 16B that controls the irradiation position in the Y axis direction. The charged particle beam of which the irradiation position is controlled by the electromagnets 16A and the electromagnets 16B is emitted to the patient side through the inside of the duct 17 of an approximately quadrangular pyramid shape.

As shown in FIG. 3, a PET unit (radiation resistance state measuring means) 14 that performs a PET scan for the tumor A is provided in the charged particle beam irradiation device 10. The PET unit 14 is provided to measure the radiation resistance state of the tumor A. The PET unit 14 measures the radiation resistance state of the tumor A immediately before the irradiation of the charged particle beam. The PET unit 14 may measure the radiation resistance state of the tumor A during the irradiation or after the irradiation.

Figure 5:
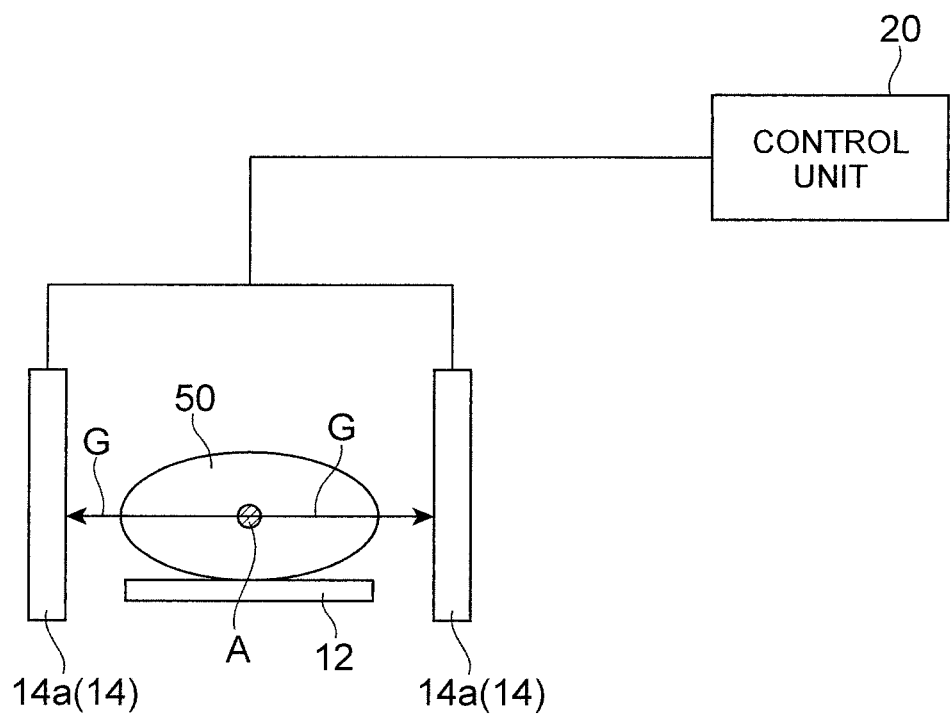
FIG. 5 is a diagram illustrating a PET scan in a charged particle beam irradiation device.

FIG. 5 is a diagram illustrating the PET scan in the charged particle beam irradiation device 10. As shown in FIGS. 3 and 5, the PET unit 14 includes a pair of gamma-ray detecting sections (gamma-ray detectors) 14a. The pair of gamma-ray detecting sections 14a is retracted to positions beside the irradiation unit 13 when not used, and is protruded for use up to positions where a patient 50 on the treatment stand 12 is disposed therebetween when the PET scan is performed.

The PET unit 14 may be configured so that the gamma-ray detecting sections 14a are not necessarily retracted to the positions beside the irradiation unit 13 when not used. For example, the PET unit 14 may be accommodated on a rear side of the gantry 11 in a rotation axis direction, or may be installed on the outside (for example, a room) of the gantry 11 instead of the inside of the gantry 11 and may be moved close to the patient within the gantry 11 when used.

The PET unit 14 detects a gamma-ray G emitted according to collapse of a radioactive tracer administered to the patient 50 by a pair of gamma-ray detecting section 14a to measure the radiation resistance state of the tumor A. As the radioactive tracer, for example, FMISO may be used.

Next, a control system of the charged particle beam irradiation device 10 will be described. A control unit 20 shown in FIGS. 3 and 4 creates a charged particle beam irradiation plan (therapy plan) in the charged particle beam irradiation device 10, and performs a charged particle beam irradiation control according to the irradiation plan. The control unit 20 performs data reading of the pre-irradiation plan created by the irradiation planning unit 6 before the therapy in the charged particle beam irradiation device 10 is performed.

The control unit 20 includes a radiation resistance state measuring section (radiation resistance state measuring means) 21, a radiation resistance region dividing section (region dividing means) 22, a radiation dose computing section (radiation dose computing means) 23, an irradiation plan correcting section (irradiation planning means) 24, and an irradiation control section 25.

The radiation resistance state measuring section 21 detects the gamma-ray emitted according to the collapse of the radioactive tracer administered to the patient and measures the radiation resistance state of the tumor A of the patient by controlling the PET unit 14. The radiation resistance state measuring section 21 inspects the position or distribution of the hypoxic cell in the tumor A by the PET unit 14 to measure the radiation resistance state of the tumor A. The radiation resistance state measuring section 21 forms the radiation resistance state measuring means disclosed in claims in combination with the PET unit 14.

Figure 2:
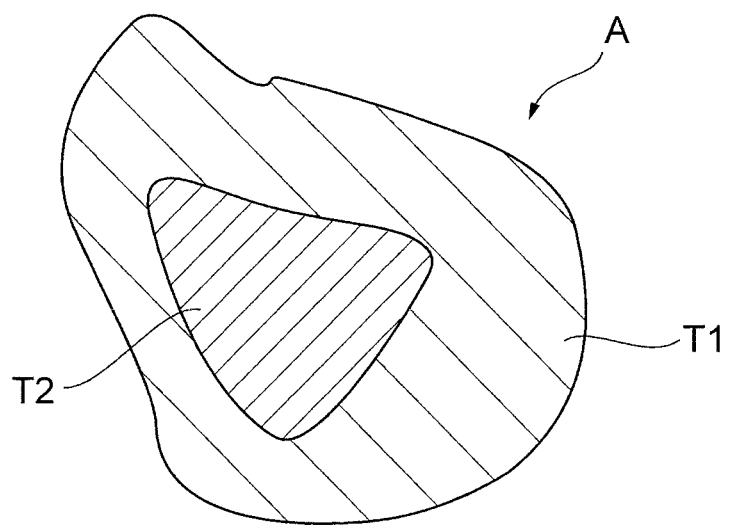
FIG. 2 is a diagram illustrating region division of a tumor.

The radiation resistance region dividing section 22 divides the tumor A into the normal radiation resistance region T1 and the high radiation resistance region T2 based on the measurement result of the radiation resistance state measuring section 21 (see FIG. 2). Since the creation of the irradiation plan in the irradiation planning unit 6 is performed several days before the actual therapy is performed, the regions T1 and T2 may not coincide with regions divided by the irradiation planning unit 6 beforehand and may be changed between the pre-inspection and the start of the actual therapy. The tumor A may be divided into three or more radiation resistance regions according to a distribution density or the like of the hypoxic cells in addition to the presence or absence of the hypoxic cell.

The radiation dose computing section 23 computes a planned radiation dose necessary for the therapy of each of the regions T1 and T2 divided by the radiation resistance region dividing section 22. The radiation dose computing section 23 performs the computation so that a planned radiation dose of the high radiation resistance region T2 is larger than a planned radiation dose of the normal radiation resistance region T1.

The radiation dose computing section 23 may perform the computation in consideration of the shape and the like of the tumor A, using an x-ray image of the tumor A captured by x-ray photographing section (not shown) or the like provided in the charged particle beam irradiation device 10.

The irradiation plan correcting section 24 creates an actual irradiation plan (therapy plan) for irradiating the tumor A with the charged particle beam. The irradiation plan correcting section 24 corrects the pre-irradiation plan based on the computation result of the radiation dose computing section 8 to create the actual irradiation plan. The number of corrections is not limited to one, and plural corrections may be performed. Thus, it is possible to create the irradiation plan in consideration of the radiation resistance of the tumor A for the patient immediately before the therapy.

The irradiation plan correcting section 24 creates an irradiation plan for defining the irradiation of the charged particle beam based on the radiation resistance state. That is, the irradiation plan correcting section 24 creates the plan so that the region T2 with high radiation resistance is irradiated with a high radiation dose, compared with the region T1 with low radiation resistance. Hereinafter, an example of the irradiation based on the radiation resistance state will be described with reference to FIGS. 6, 7A and 7B. The irradiation based on the radiation resistance state is not limited to FIGS. 6, 7A and 7B.

Figure 6:
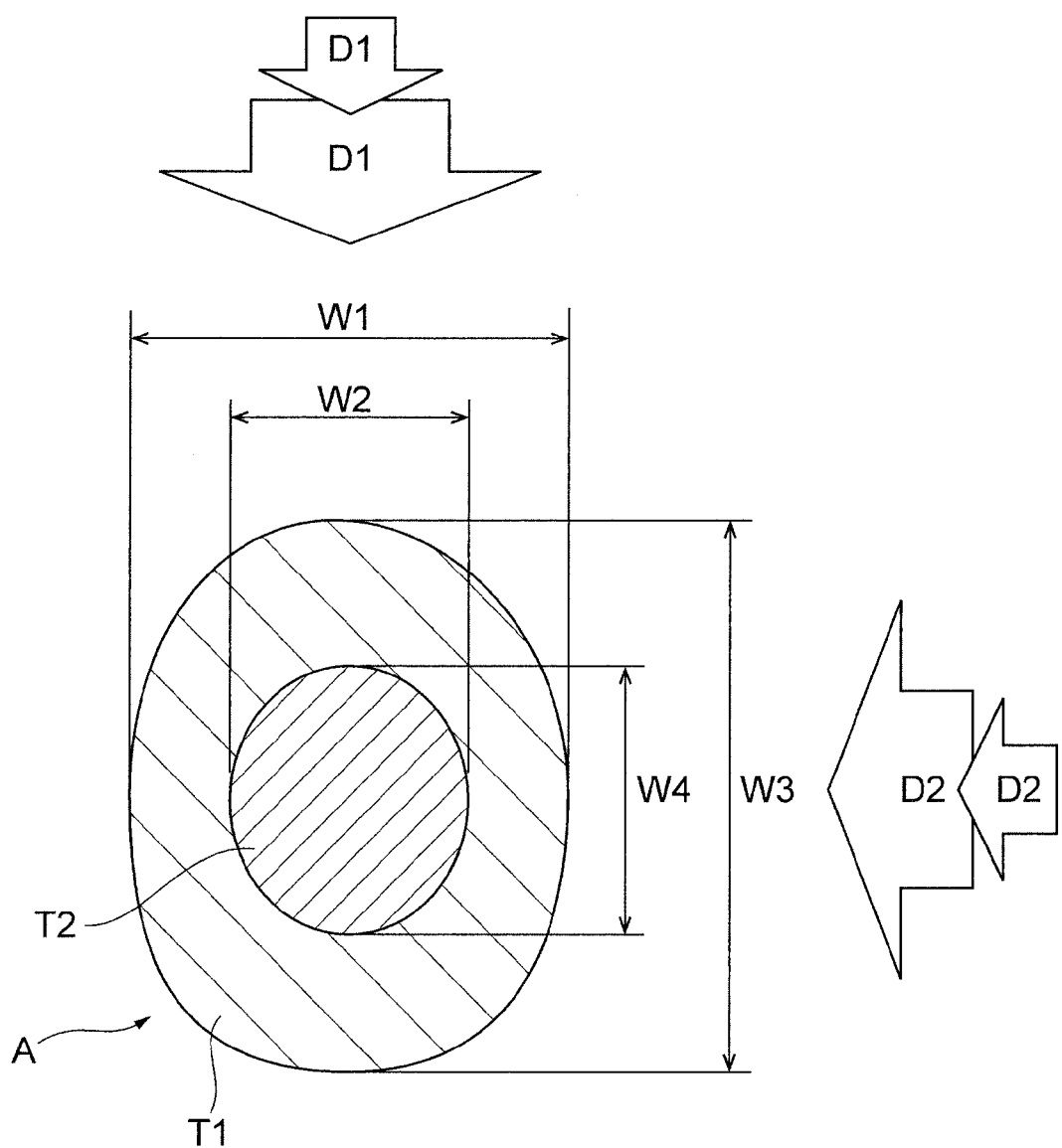
FIG. 6 is a diagram illustrating irradiation based on radiation resistance.

FIG. 6 is a diagram illustrating change in the number of irradiations based on the radiation resistance state. As shown in FIG. 6, as the irradiation based on the radiation resistance state, for example, a method of increasing the number of irradiations for the region T2 with high radiation resistance compared with the region T1 with low radiation resistance is used. In this irradiation, an irradiation angle of the irradiation unit 13 is adjusted by the rotation of the gantry 11, so that the irradiation of the charged particle beams is performed in plural directions (for example, direction D1 and direction D2).

In FIG. 6, when seen in the direction D1, an irradiation field corresponding to the region T1 is indicated as W1, and an irradiation field corresponding to the region T2 is indicated as W2. Similarly, when seen in the direction D2, an irradiation field corresponding to the region T1 is indicated as W3, and an irradiation field corresponding to the region T2 is indicated as W4. The irradiation field W1 includes the irradiation field W2, and the irradiation field W3 includes the irradiation field W4.

In this irradiation, the irradiation in the irradiation field W1 and the irradiation in the irradiation field W2 are respectively performed for the tumor A in the direction D1. Further, the irradiation in the irradiation field W3 and the irradiation in the irradiation field W4 are respectively performed in the direction D2.

In this way, by increasing the number of irradiations for the region T2 with high radiation resistance compared with the region T1 with low radiation resistance, it is possible to realize the irradiation with the radiation dose based on the radiation resistance state. In this case, in the irradiation of the irradiation fields W1, W2, W3 and W4, the irradiation conditions of the irradiation unit 13 are controlled based on the computation result of the radiation dose computing section 8 for each of the regions T1 and T2.

FIGS. 7A and 7B are diagrams illustrating intensity-modulated ion therapy based on the radiation resistance state. FIG. 7A is a diagram illustrating intensity-modulated ion therapy in the direction D1, and FIG. 7B is a diagram illustrating intensity-modulated ion therapy in the direction D2. As shown in FIGS. 7A and 7B, in the intensity-modulated ion therapy, the irradiation angle of the irradiation unit 13 is adjusted by the rotation of the gantry 11, so that the emission of the charged particle beam is performed in different plural directions (for example, direction D1 and direction D2). Here, in the intensity-modulated ion therapy, the scan rate or the like of the charged particle beam is controlled so that the radiation dose set for each irradiation region is satisfied. Here, the radiation dose may be changed while maintaining the scan rate to be constant.

In FIG. 7A, when seen in the direction D1, an irradiation field corresponding to the region T1 is indicated as W11, and an irradiation field corresponding to the region T2 is indicated as W12. In the intensity-modulated ion therapy shown in FIG. 7A, the tumor A is divided into plural layers (layers that are orthogonal to the direction D1) in the direction D1, and the irradiation conditions are controlled for each layer based on the computation result of the radiation dose computing section 8. That is, as shown in a layer LA1 and a layer LA2, the irradiation field W11 and the irradiation field W12 are set for each layer. In the intensity-modulated ion therapy shown in FIG. 7A, the irradiation conditions are controlled so that the scan rate in the irradiation field W12 is slower than the scan rate in the irradiation field W11. Here, the irradiation conditions may be controlled so that the radiation dose for irradiation of the irradiation field W12 is higher than the radiation dose for irradiation of the irradiation field W11 while maintaining the scan rate to be constant. In the intensity-modulated ion therapy shown in FIG. 7A, the irradiation is sequentially performed from the layer on a deep part side to the layer on a shallow part side in the direction D1.

Similarly, in FIG. 7B, when seen in the direction D2, an irradiation field corresponding to the region T1 is indicated as W13, and an irradiation field corresponding to the region T2 is indicated as w14. Further, in FIG. 7B, layers LB1 and LB2 are shown. In the intensity-modulated ion therapy shown in FIG. 7B, in the respective layers that include the layers LB1 and LB2, the irradiation conditions are controlled so that the scan rate in the irradiation field W14 is slower than the scan rate in the irradiation field W13. In the intensity-modulated ion therapy shown in FIG. 7B, the irradiation is sequentially performed from the layer on a deep part side to the layer on a shallow part side in the direction D2.

By performing the intensity-modulated ion therapy as described above, it is possible to irradiate the tumor A with the charged particle beam having a sufficient radiation dose while suppressing the radiation dose received by a normal tissue. Further, since it is possible to irradiate the tumor A with the charged particle beam having an appropriate radiation dose for each of the regions T1 and T2 in consideration of the radiation resistance state of the tumor A, it is possible to realize effective therapy.

The irradiation control section 25 controls the emission of the charged particle beam from the irradiation unit 13 based on the irradiation plan created by the irradiation plan correcting section 24. The irradiation control section 25 performs the irradiation for the tumor A based on the irradiation plan.

Next, a charged particle beam irradiation planning method in the charged particle beam irradiation system 1 according to the first embodiment will be described. This charged particle beam irradiation planning method includes a pre-irradiation planning method performed by the control unit 3 and the irradiation planning unit 6 of the PET-CT device 2, and an irradiation plan correcting method performed by the control unit 20 of the charged particle beam irradiation device 10.

Figure 8:
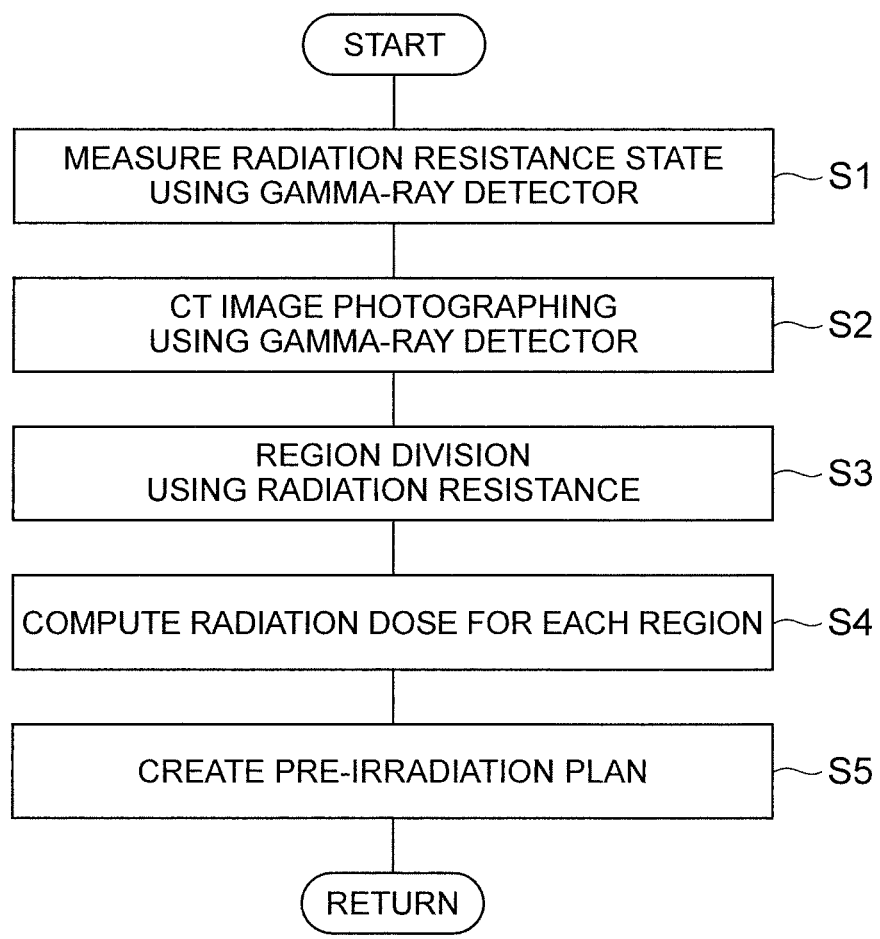
FIG. 8 is a flowchart illustrating a pre-irradiation planning method of a charged particle beam irradiation planning method according to one embodiment.

FIG. 8 is a flowchart illustrating the pre-irradiation planning method. As shown in FIG. 8, in the pre-irradiation planning method, first, in the control unit 3, a first radiation resistance state measuring step of performing a PET scan for the patient by the radiation resistance state measuring section 4 is performed (S1). In the first radiation resistance state measuring step, the PET-CT device 2 is controlled by the control unit 3, so that the gamma-ray emitted according to the collapse of the radioactive tracer administered to the patient is detected and the radiation resistance state (hypoxic cell) of the tumor A is measured.

Then, a CT image capturing step of performing a CT scan for the patient as the CT image capturing section 5 controls the PET-CT device 2 is performed (S2). In the image capturing step, a tomogram of the tumor A using X rays or the like is captured.

Subsequently, in the irradiation planning unit 6, a first region dividing step is performed by the radiation resistance region dividing section 7 (S3). In the first region dividing step, the tumor A is divided into the normal radiation resistance region T1 and the high radiation resistance region T2 based on the measurement result of the first radiation resistance state measuring step. The tumor A may be divided into two or more regions based on the measurement result of the radiation resistance state.

Subsequently, in the irradiation planning unit 6, a first radiation dose computing step is performed by the radiation dose computing section 8 (S4). In the first radiation dose computing step, a planned radiation dose necessary for therapy for each of the regions T1 and T2 divided in the first region dividing step is computed.

Then, in the irradiation planning unit 6, a pre-irradiation planning step is performed by the pre-irradiation planning section 9 (S5). In the pre-irradiation planning step, a pre-irradiation plan is created based on the computation result of the first radiation dose planning step and the shape and the like of the tumor A obtained from the tomogram of the tumor A. In the pre-irradiation planning step, a pre-irradiation plan of the intensity-modulated ion therapy is created. In the pre-irradiation plan, the irradiation directions of the charged particle beam, the scan rate of the charged particle beam for each of the regions T1 and T2, and the like are determined.

Figure 9:
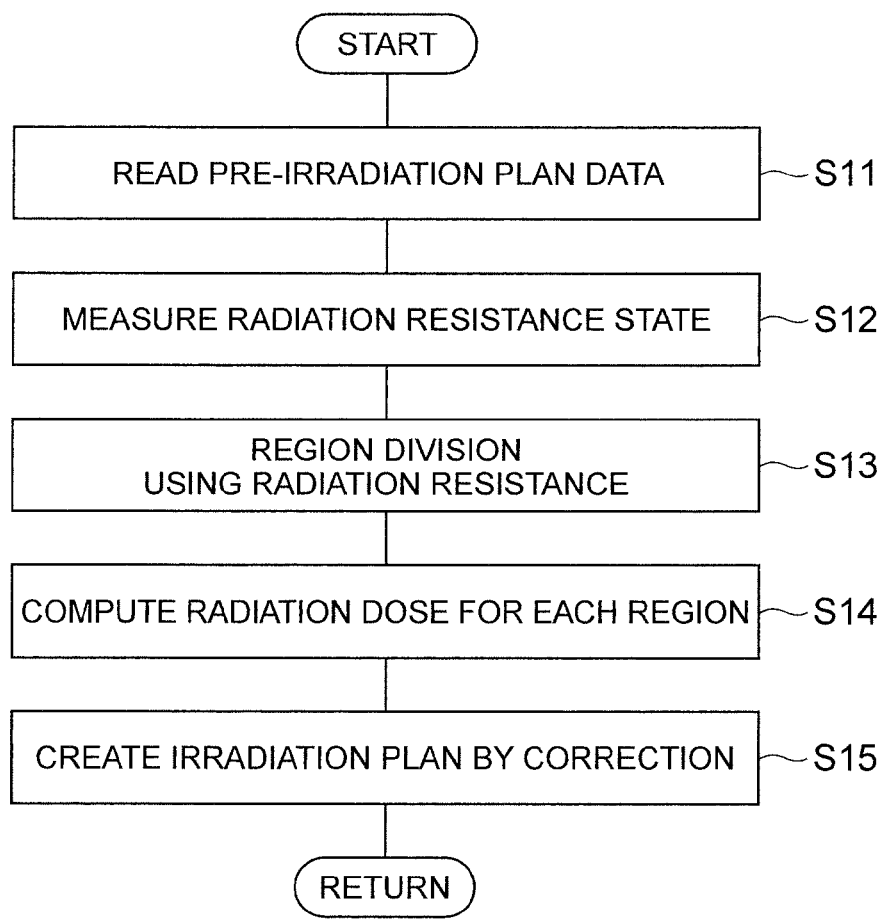
FIG. 9 is a flowchart illustrating an irradiation plan correcting method of the charged particle beam irradiation planning method according to one embodiment.

FIG. 9 is a flowchart illustrating an irradiation plan correcting method in the control unit 20 of the charged particle beam irradiation device 10. As shown in FIG. 9, in the irradiation plan correcting method, in the control unit 20 of the charged particle beam irradiation device 10, a plan data reading step of reading data on the pre-irradiation plan planned by the irradiation planning unit 6 is performed (S11).

Next, a second radiation resistance state measuring step is performed by the radiation resistance state measuring section 21 (S12). In the second radiation resistance state measuring step, the radiation resistance state of the tumor A of the patient on the treatment stand 12 is measured. Specifically, the radiation resistance state measuring section 21 detects the gamma-ray emitted according to the collapse of the radioactive tracer administered to the patient by the PET unit 14 to measure the radiation resistance state (hypoxic cell).

Subsequently, a second region dividing step is performed by the radiation resistance region dividing section 22 (S13). In the second region dividing step, the region division of the tumor A is performed based on the measurement result of the second radiation resistance state measuring step. In the second region dividing step, the tumor A is divided into the normal radiation resistance region T1 and the high radiation resistance region T2.

Then, a second radiation dose computing step is performed by the radiation dose computing section 23 (S14). In the second radiation dose computing step, the radiation dose computing section 23 computes a planned radiation dose necessary for therapy of each of the regions T1 and T2 divided in the second region dividing step. The radiation dose computing section 23 performs the computation so that a planned radiation dose of the high radiation resistance region T2 is larger than a planned radiation dose of the normal radiation resistance region T1. In the second radiation dose computing step, the planed radiation dose is computed based on the density or the like of the hypoxic cells included in each of the regions T1 and T2.

Subsequently, an irradiation planning step is performed by the irradiation plan correcting section 24 (S15). In the irradiation planning step, an irradiation plan to be performed in practice by correcting the pre-irradiation plan created by the irradiation planning unit 6 is created based on the computation result of the second radiation dose computing step. In the irradiation planning step, an irradiation plan of the intensity-modulated ion therapy of the charged particle beam with respect to the tumor A of the patient is created.

According to the charged particle beam irradiation system 1 and the charged particle beam irradiation planning method according to the present embodiment described above, since the radiation dose for irradiation is changed according to the level (radiation resistance state) of the radiation resistance, by dividing the tumor A into the plural regions T1 and T2 according to the level of the radiation resistance, it is possible to compute an appropriate planned radiation dose for each region, thereby creating an effective irradiation plan of the charged particle beam. Further, in the charged particle beam irradiation system 1 and the charged particle beam irradiation planning method, by creating the intensity-modulated ion therapy plan, it is possible to reduce the influence on a normal tissue around the tumor A due to the irradiation of the charged particle beam. Further, according to the charged particle beam irradiation system 1 and the charged particle beam irradiation planning method, by computing the beam intensity of the charged particle beam at each irradiation angle based on the planned radiation dose computed for each region, it is possible to create an irradiation plan of the charged particle beam with an excellent therapy effect in consideration of the radiation resistance.

Further, according to the charged particle beam irradiation system 1 and the charged particle beam irradiation planning method according to the present embodiment, by detecting the accumulation of the radioactive tracer by the PET-CT device 2 or the PET unit 14 of the charged particle beam irradiation device 10, it is possible to measure the presence or absence or distribution of the hypoxic cells with high radiation resistance compared with the normal lesion cell. Accordingly, according to the charged particle beam irradiation system 1 and the charged particle beam irradiation planning method according to the present embodiment, it is possible to achieve the region division of the tumor A according to the level of the radiation resistance with reference to the presence or absence, distribution or the like of the hypoxic cells.

Further, in the charged particle beam irradiation system 1 and the charged particle beam irradiation planning method according to the present embodiment, the pre-irradiation plan is created in advance based on the results of the PET scan and the CT scan that are performed in advance. Then, by measuring the radiation resistance state of the tumor A at a point in time when it is actually irradiated with the charged particle beam, it is possible to correct the pre-irradiation plan based on the planned radiation dose computed for each of the regions T1 and T2 according to the radiation resistance state, to thereby create the irradiation plan to be performed in practice.

Accordingly, according to the charged particle beam irradiation system 1 and the charged particle beam irradiation planning method according to the present embodiment, it is possible to measure the radiation resistance state of the tumor A in a state where the patient is disposed on the treatment stand 12 when actually irradiated with the charged particle beam, and to reflect the measurement result to the irradiation plan. Thus, it is possible create a more effective irradiation plan of the charged particle beam.

Second Embodiment

A charged particle beam irradiation system 31 according to a second embodiment is different from the charged particle beam irradiation system 1 according to the first embodiment in that an irradiation plan to be performed in practice is created only by an irradiation planning unit 32. The same configurations as those of the charged particle beam irradiation system 1 according to the first embodiment are given the same reference numerals, and description thereof will not be repeated.

Figure 10:
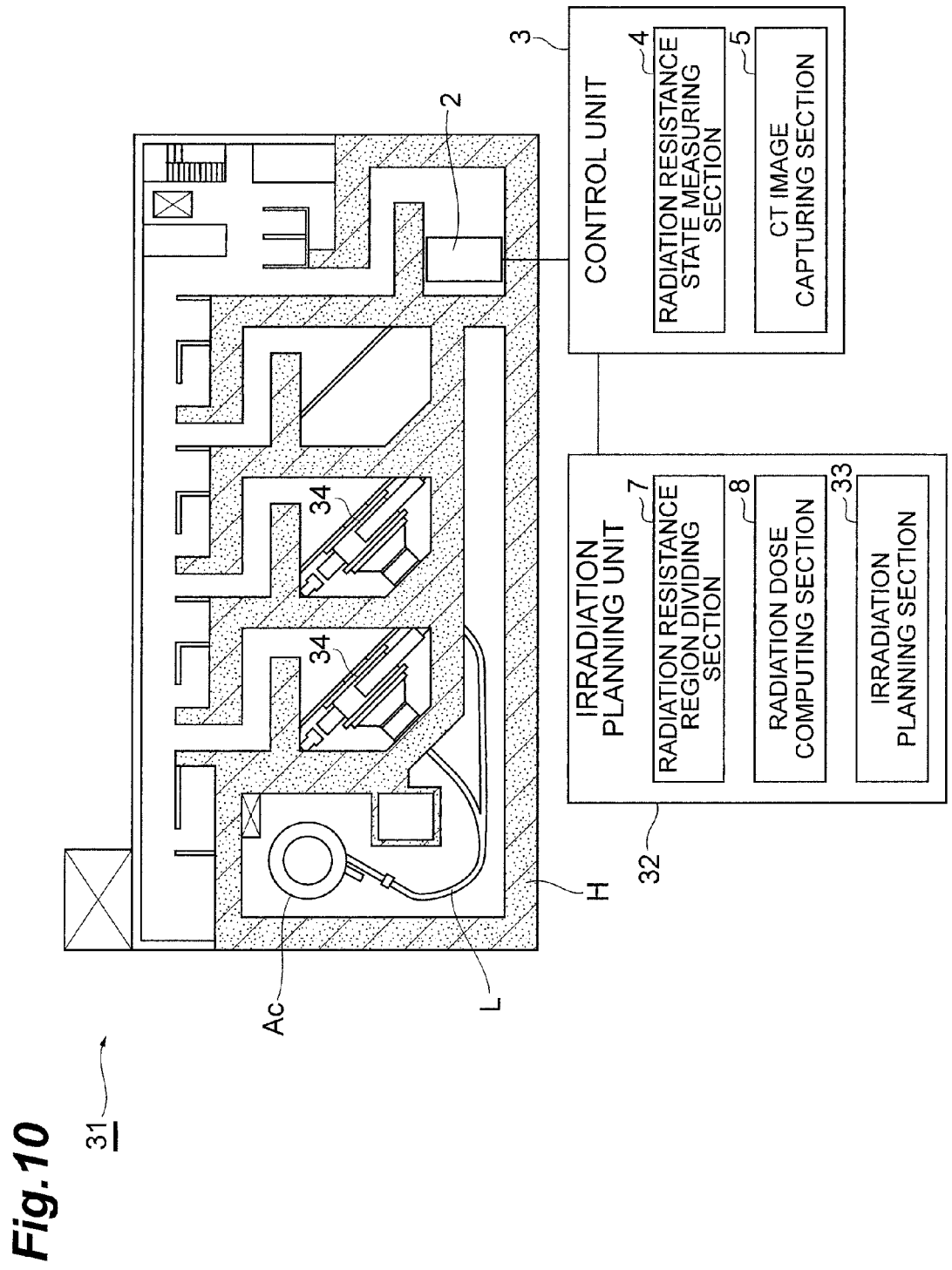
FIG. 10 is a diagram schematically illustrating a charged particle beam irradiation system according to another embodiment.

FIG. 10 is a schematic view illustrating the charged particle beam irradiation system 31 according to the second embodiment. As shown in FIG. 10, the charged particle beam irradiation system 31 according to the second embodiment includes the irradiation planning unit 32. In the irradiation planning unit 32 according to the second embodiment, an irradiation plan of defining irradiation to be performed at an actual treatment date is created based on the results of the PET scan and the CT scan of the PET-CT device 2 performed in advance.

The irradiation planning unit 32 includes an irradiation planning section 33 instead of the pre-irradiation planning section 9 according to the first embodiment. The irradiation planning section 33 creates an irradiation plan based on the shape and the like of the tumor A obtained from the tomogram of the tumor A by the PET-CT device 2 and the computation result of the radiation dose computing section 8.

On the other hand, a charged particle beam irradiation device 34 according to the second embodiment executes irradiation of a charged particle beam for the tumor A based on the irradiation plan planned by the irradiation planning unit 32. The charged particle beam irradiation device 34 does not perform the correction of the irradiation plan based on the measurement result of the radiation resistance state of the tumor A immediately before treatment.

In the charged particle beam irradiation system 31 according to the second embodiment, the PET-CT device 2 and the radiation resistance state measuring section 4 of the control unit 3 form the radiation resistance state measuring means. Further, the radiation resistance region dividing section 7 of the irradiation planning unit 32 forms the region dividing means. Similarly, the radiation dose computing section 8 of the irradiation planning unit 32 forms the radiation dose computing means. Further, the irradiation planning section 33 of the irradiation planning unit 32 forms the irradiation planning means.

Figure 11:
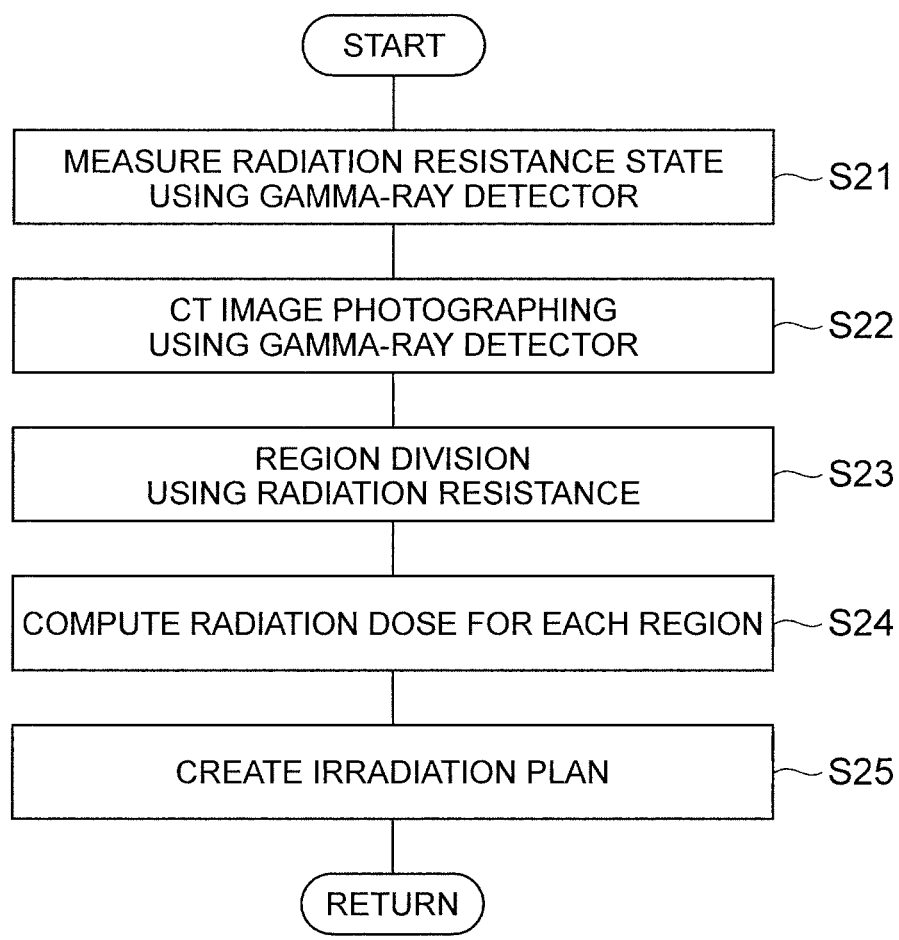
FIG. 11 is a flowchart illustrating a charged particle beam irradiation planning method according to another embodiment.

Next, a charged particle beam irradiation planning method in the charged particle beam irradiation system 31 according to the second embodiment will be described. FIG. 11 is a flowchart illustrating the charged particle beam irradiation planning method according to the second embodiment. Since steps S21 to S24 are the same as steps S1 to S4 of the charged particle beam irradiation planning method according to the first embodiment, detailed description will not be repeated.

As shown in FIG. 11, in the charged particle beam irradiation planning method according to the second embodiment, first, in the control unit 3 of the PET-CT device 2, a radiation resistance state measuring step of performing the PET scan for the patient using the radiation resistance state measuring section 4 is performed (S21). Then, in the control unit 3 of the PET-CT device 2, a CT image capturing step of performing the CT scan for the patient using the CT image capturing section 5 is performed (S22).

Subsequently, in the irradiation planning unit 32, a region dividing step is performed by the radiation resistance region dividing section 7 (S23). In the region dividing step, the region division of the tumor A based on the measurement result of the radiation resistance state measurement step is performed. Then, in the irradiation planning unit 32, a radiation dose computing step is performed by the radiation dose computing section 8 (S24). In the radiation dose computing step, a planned radiation dose for each region of the tumor A divided in the region dividing step is computed.

Subsequently, in the irradiation planning unit 32, an irradiation planning step is performed by the irradiation planning section 33 (S25). In the irradiation planning step, the irradiation plan is created based on the computation result of the radiation dose computing step and the shape and the like of the tumor A obtained from the tomogram of the tumor A. In the irradiation planning step, the irradiation plan of the intensity-modulated ion therapy is created.

According to the charged particle beam irradiation system 31 and the charged particle beam irradiation planning method according to the above-described second embodiment, since it is possible to create an actual irradiation plan in detail in advance based on the planned value of the radiation dose for each region computed from the radiation resistance state of the tumor A and the captured image of the tumor A obtained by the CT scan, it is possible to create an effective irradiation plan of the charged particle beam in consideration of the radiation resistance even when the inspection unit such as a PET unit is installed in a room other than an irradiation room.

The present invention is not limited to the above-described embodiments.

For example, the charged particle beam irradiation system and the charged particle beam irradiation planning method according to the embodiments of the present invention are not limited to a charged particle beam irradiation of a scanning type, and for example, may be applied to a charged particle beam irradiation of a multi-patch type.

Figure 12:
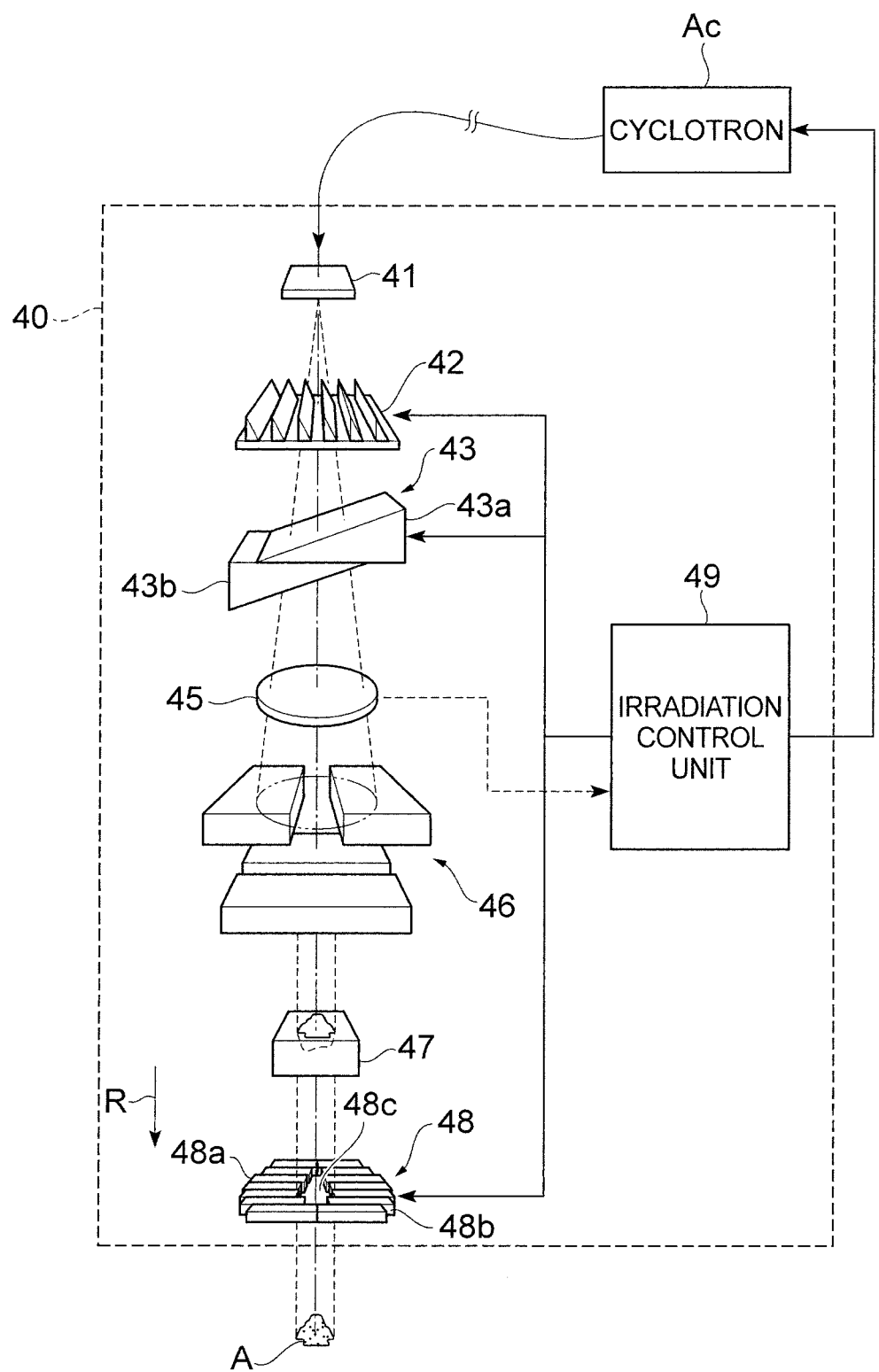
FIG. 12 is a diagram illustrating an irradiation device of a charged particle beam of a multi-patch type.

FIG. 12 is a diagram illustrating a charged particle beam irradiation device of a multi-patch type. An irradiation device 40 of the multi-patch type shown in FIG. 12 includes a scatterer 41, a ridge filter 42, a fine-scale degrader 43, a radiation dose monitor 45, a block collimator 46, a bolus 47, and a multi-leaf collimator 48 that are sequentially arranged in a charged particle beam irradiation direction R. Further, the irradiation device 40 includes an irradiation control unit 49 that controls driving of the respective units of the device.

The irradiation device 40 allows the charged particle beam transmitted from the accelerator Ac to pass through the scatterer 41 to expand in a direction orthogonal to the irradiation direction R, to thereby be enlarged a beam of a wide range. Then, the charged particle beam incident onto the ridge filter 42 forms a spread-out Bragg peak distribution in the irradiation direction R.

The charged particle beam passed through the ridge filter 42 is incident onto the fine-scale degrader 43 for adjusting the maximum arrival depth of the charged particle beam based on the depth of the tumor A in the patient. The fine-scale degrader 43 includes two wedge-shaped blocks 43a and 43b that face each other, for example. By adjusting the overlapping way of the blocks 43a and 43b under the control of the irradiation control unit 49, it is possible to continuously change the thickness of a portion through which the charged particle beam passes. By adjusting the fine-scale degrader 43, the position of the spread-out Bragg peak of the charged particle beam is adjusted in the depth direction (irradiation direction R) of the tumor A in the patient.

The radiation dose of the charged particle beam passed through the fine-scale degrader 43 is detected in the radiation dose monitor 45. Then, the charged particle beam is incident onto the block collimator 46 for roughly shaping the planar shape (shape seen in the irradiation direction R) of the charged particle beam. Then, the charged particle beam is incident to the bolus 47, in which correction relating to a cross-sectional shape of the maximum depth of the tumor A and non-uniformity of the tissue is performed.

The charged particle beam passed through the bolus 47 is incident onto the multi-leaf collimator 48. The multi-leaf collimator 48 is configured by two shielding portions 48a and 48b having multiple comb teeth of a width of several millimeters, in which the shielding portions 48a and 48b are arranged to abut each other at tips of the comb teeth. Further, the plural comb teeth of the shielding portions 48a and 48b advance and retract in the length direction, respectively, under the control of the irradiation control unit 49. Thus, the multi-leaf collimator 48 can change the position and shape of an opening 48c through which the charged particle beam passes.

Figure 13:
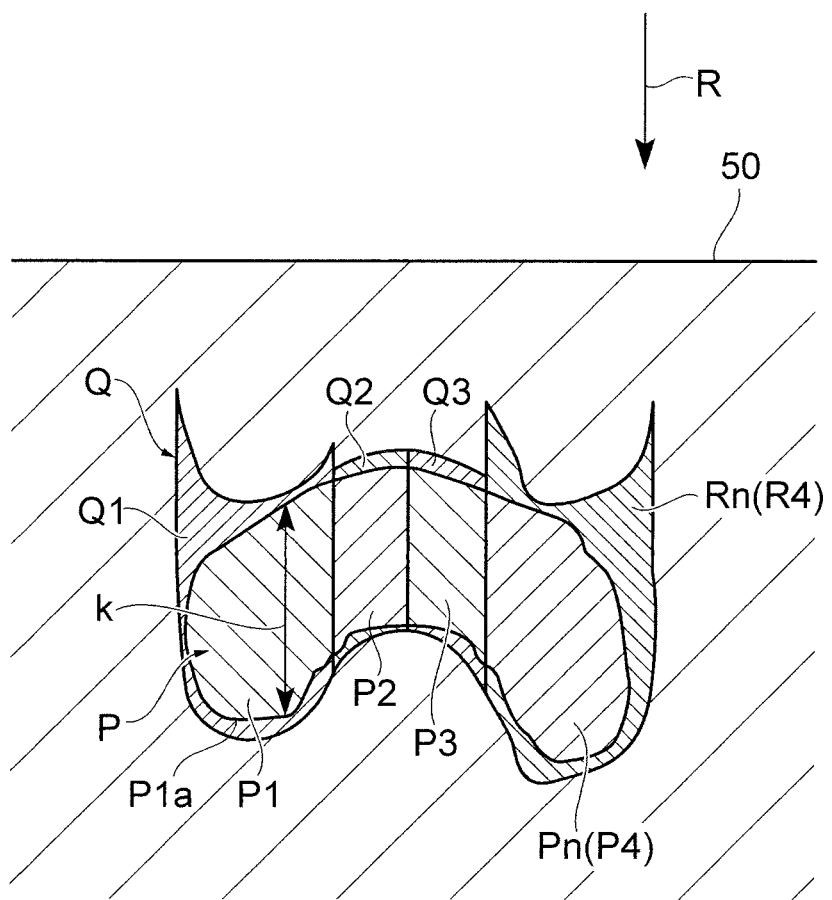
FIG. 13 is a diagram illustrating irradiation of a charged particle beam of a multi-patch type.

Subsequently, the charged particle beam irradiation of the multi-patch type will be described with reference to FIG. 13. As shown in FIG. 13, the control unit 49 divides a tumor P into plural blocks based on a three-dimensional shape of the tumor P. In the control unit 49, planar positions and planar shapes of first to n-th divided blocks P1 to Pn, arrangement of the divided blocks P1 to Pn in a depth direction, and radiation doses of charged particle beams for irradiation of the divided blocks P1 to Pn are provided as data, in association. Arrangement information of the divided blocks P1 to Pn in the depth direction includes information about the depth of the deepest portion of the divided blocks, the depth of the shallowest portion thereof, the maximum thickness in the depth direction and the like. Further, in FIG. 13, an example in which the number of divided blocks is n=4 is shown, but n may be set to an arbitrary number.

The control unit 49 reads the information about the planar position and the planar shape of the first divided block P1, drives the multi-leaf collimator 48 to form the opening 48c of the multi-leaf collimator 48 to have a planar position and a planar shape corresponding to the first divided block P1. Thus, it is possible to set a planar position and a planar shape of an irradiation field that is extended slightly outside from a contour of the first divided block P1. Further, the control unit 49 drives the fine-scale degrader 43 so that the maximum arrival depth of a proton beam reaches a position that is slightly deeper than the deepest portion P1a of the first divided block P1.

Further, the control unit 49 reads information about the maximum thickness k of the first divided block P1 of the tumor P in the depth direction, and drives the ridge filter 42 so that a spread-out Bragg peak (SOBP) width of the proton beam is slightly larger than the maximum thickness k that adjusts the SOBP. Due to the operations of the respective units as described above, a first divided irradiation range Q1 that forms a shape including the three-dimensional shape of the first divided block P1 of the tumor P is set. Further, the control unit 49 computes a radiation dose for irradiation of the first divided irradiation range Q1.

In this state, if the charged particle beam is transmitted to the irradiation device 40, the first divided irradiation range Q1 is irradiated with the charged particle beam, and particle beam energy is collectively supplied to the first divided block P1 of the tumor P. Here, the control unit 49 receives a monitor signal from the radiation dose monitor 45 to detect the radiation dose of the charged particle beam that irradiates the first divided irradiation range Q1. Further, when the radiation dose of the detected charged particle beam reaches a planned radiation dose, the supply of the charged particle beam is stopped. According to such a process, the first divided irradiation range Q1 is irradiated with a radiation dose based on the irradiation plan. Further, by repeating the irradiation operation n times with respect to each of the first to n-th divided blocks P1 to Pn, it is possible to irradiate the entire tumor P with the charged particle beam while sequentially setting the first to n-th divided irradiation fields R1 to Rn corresponding to the three-dimensional shapes of each of the divided blocks P1 to Pn.

In the above-described multi-patch type irradiation, the tumor P is divided into the plural blocks and the irradiation conditions are controlled. Thus, in the multi-patch type irradiation, by measuring the radiation resistance state of the tumor P and performing the block division (region division) based on the radiation resistance, it is possible to achieve the irradiation with a radiation dose in consideration of the radiation resistance with respect to each block.

Further, in the embodiments of the present invention, the radiation resistance state of the tumor A may be measured based on conditions other than the presence or absence of the hypoxic cells or distribution thereof. As a tracer for measuring the radiation resistance state (hypoxic cell), FAZA, IAZA, FETNIM, FETA, ATSM, β-5-FAZR, [$^{18}$F]EF5, [$^{18}$F]EF3, [$^{18}$F]FDG or the like, in addition to FMISO, may be employed.

For example, since FAZA has low fat-solubility and quick blood clearance compared with FMISO, it is possible to perform more effective measurement of the hypoxic cell. Further, in a PET image when FETNIM is used, it is possible to reduce the background of the tumor compared with FMISO.

Further, the embodiments of the present invention may be applied to intensity-modulated ion therapy using spot scanning, in addition to the intensity-modulated ion therapy using the raster scanning or line scanning. Further, the gantry 11 is not necessarily rotatable at an angle of 360°, and may be configured to oscillate at an angle smaller than 360°. Further, the gantry may be a fixed type.

Further, the quadrupole magnet 15 and/or the duct 17 may not be installed in the irradiation unit 13. Further, the number of the gamma-ray detecting sections provided in the PET unit 14 is not limited to two, and may be three or more. Further, the gamma-ray detecting means is not limited to the PET, and single photon emission computed tomography (SPECT) or the like may be used. In the case of SPECT, a single gamma-ray detecting section may be used.

Further, in the charged particle beam irradiation device, a configuration in which the PET scan and the CT scan are performed during treatment and the irradiation plan is created in this state is also included in the embodiments of the present invention.

Further, during irradiation of the charged particle beam (during treatment), the gamma-ray emitted from the affected part A of the patient may be detected using the PET unit 14. If the affected part A of the patient is irradiated with the charged particle beam (for example, proton beam), the gamma-ray is emitted from a positron emitter generated by nuclear reaction of an incident proton nucleus of the irradiating proton beam and an atomic nucleus in the tumor. By detecting the gamma-ray by the PET unit 14, it is possible to measure the position irradiated with the proton beam. When the measured proton beam irradiation position is different from an irradiation position defined in a therapy plan, the control unit 20 may control the irradiation unit 13 so that an actual proton beam irradiation position becomes the irradiation position defined in the therapy plan. As described above, by using the PET unit used for creation of the therapy plan as the PET unit that confirms the irradiation position of the charged particle beam, it is not necessary to provide two PET units in the charged particle beam irradiation device 10. Thus, it is possible to simplify the device to reduce the cost.

The invention may be used for a charged particle beam irradiation system and a charged particle beam irradiation planning method capable of creating an irradiation plan of a charged particle beam in consideration of radiation resistance.

It should be understood that the invention is not limited to the above-described embodiment, but may be modified into various forms based on the spirit of the invention. Additionally, the modifications are included in the scope of the invention.

What is claimed is:

1. A charged particle beam irradiation system comprising:
an irradiation unit configured to irradiate an irradiation target with a charged particle beam;
a radiation resistance state measuring section configured to measure a radiation resistance state of the irradiation target;
a region dividing section configured to divide the irradiation target into a plurality of radiation resistance regions based on a measurement result of the radiation resistance state measuring section;
a radiation dose computing section configured to compute a planned value of a radiation dose of the charged particle beam for each of the plurality of radiation resistance regions divided by the region dividing section; and
an irradiation planning section configured to create an irradiation plan of the charged particle beam with respect to the irradiation target based on a computation result of the radiation dose computing section.

2. The charged particle beam irradiation system according to claim 1, further comprising:
a pre-irradiation planning section configured to create a pre-irradiation plan of the charged particle beam with respect to the irradiation target based on a captured image of the irradiation target,
wherein the irradiation planning section corrects the pre-irradiation plan based on the computation result of the radiation dose computing section to create the irradiation plan.

3. The charged particle beam irradiation system according to claim 1,
wherein the irradiation planning section creates the irradiation plan based on a captured image of the irradiation target and the computation result of the radiation dose computing section.

4. The charged particle beam irradiation system according to claim 1,
wherein the radiation resistance state measuring section includes a gamma-ray detector, and
wherein the region dividing section divides the irradiation target into the plurality of radiation resistance regions based on a measurement result of the gamma-ray detector that uses FMISO as a tracer.

5. The charged particle beam irradiation system according to claim 1,
wherein the radiation resistance state measuring section includes a gamma-ray detector, and
wherein the region dividing section divides the irradiation target into the plurality of radiation resistance regions based on a measurement result of the gamma-ray detector that uses FAZA as a tracer.

6. The charged particle beam irradiation system according to claim 1,
wherein the radiation resistance state measuring section includes a gamma-ray detector, and
wherein the region dividing section divides the irradiation target into the plurality of radiation resistance regions based on a measurement result of the gamma-ray detector that uses IAZA as a tracer.

7. The charged particle beam irradiation system according to claim 1,
wherein the radiation resistance state measuring section includes a gamma-ray detector, and
wherein the region dividing section divides the irradiation target into the plurality of radiation resistance regions based on a measurement result of the gamma-ray detector that uses FETNIM as a tracer.

8. A charged particle beam irradiation planning method comprising:
a radiation resistance state measuring step of measuring a radiation resistance state of an irradiation target;
a region dividing step of dividing the irradiation target into a plurality of radiation resistance regions based on a measurement result of the radiation resistance state measuring step;
a radiation dose computing step of computing a planned value of a radiation dose of a charged particle beam for each of the plurality of radiation resistance regions divided in the region dividing step; and
an irradiation planning step of creating the irradiation plan of the charged particle beam with respect to the irradiation target based on a computation result of the radiation dose computing step.

9. The charged particle beam irradiation planning method according to claim 8, further comprising:
a pre-irradiation planning step of creating a pre-irradiation plan of the charged particle beam with respect to the irradiation target based on a captured image of the irradiation target before the radiation resistance state measuring step,
wherein in the irradiation planning step, the pre-irradiation plan is corrected based on the computation result of the radiation dose computing step to create the irradiation plan.

10. The charged particle beam irradiation planning method according to claim 8,
wherein in the irradiation planning step, the irradiation plan is created based on a captured image of the irradiation target and the computation result of the radiation dose computing step.

11. The charged particle beam irradiation planning method according to claim 8,
wherein in the radiation resistance state measuring step, the radiation resistance state of the irradiation target is measured based on a gamma-ray detection that uses FMISO as a tracer.

12. The charged particle beam irradiation planning method according to claim 8,
wherein in the radiation resistance state measuring step, the radiation resistance state of the irradiation target is measured based on a gamma-ray detection that uses FAZA as a tracer.

13. The charged particle beam irradiation planning method according claim 8,
wherein in the radiation resistance state measuring step, the radiation resistance state of the irradiation target is measured based on a gamma-ray detection that uses IAZA as a tracer.

14. The charged particle beam irradiation planning method according to claim 8,
wherein in the radiation resistance state measuring step, the radiation resistance state of the irradiation target is measured based on a gamma-ray detection that uses FETNIM as a tracer.

* * * * *